United States Patent [19]

Lover et al.

[11] Patent Number: 4,491,576

[45] Date of Patent: Jan. 1, 1985

[54] POLYOXYETHYLENE DERIVATIVES AS ANTIPRURITIC ECTOPARASITICIDE

[75] Inventors: Myron J. Lover, Mountainside; Arnold J. Singer, South Orange; Donald M. Lynch, Waldwick; William E. Rhodes, III, Cranford, all of N.J.

[73] Assignee: Block Drug Company, Inc., Jersey City, N.J.

[21] Appl. No.: 429,457

[22] Filed: Sep. 30, 1982

Related U.S. Application Data

[60] Division of Ser. No. 4,229, Jan. 17, 1979, Pat. No. 4,372,977, which is a continuation of Ser. No. 802,012, May 31, 1977, abandoned.

[51] Int. Cl.$^3$ ............................................. A61K 31/74
[52] U.S. Cl. ..................................................... 424/78
[58] Field of Search .......................................... 424/78

[56] References Cited

U.S. PATENT DOCUMENTS

| Re. 29,909 | 2/1979 | Kurtz | 424/78 |
| 2,666,728 | 1/1954 | Smith | 424/299 |
| 2,898,267 | 8/1959 | Lindner | 424/342 |

OTHER PUBLICATIONS

Wigglesworth, V. B., Transpiration Through the Cuticle of Insects, Journal of Experimental Biology, 21, 3, 4, p. 97, (1945).

Maxwell and Piper, Molecular Structure of Nonionic Surfactants in Relation to Laboratory Insecticidal Activity, Journal of Economic Entomology, 61, No. 6, Dec. 1968, p. 1633.

*Primary Examiner*—Allen J. Robinson
*Attorney, Agent, or Firm*—Ostrolenk, Faber, Gerb & Soffen

[57] ABSTRACT

Certain ethoxylates have been found to exhibit concurrent activities of particular merit in the treatment of ectoparasitic infestations.

11 Claims, No Drawings

POLYOXYETHYLENE DERIVATIVES AS ANTIPRURITIC ECTOPARASITICIDE

This is a divison of application Ser. No. 4,229 filed Jan. 17, 1979 now U.S. Pat. No. 4,372,977 which in turn is a continuation of application Ser. No. 802,012 filed May 31, 1977 now abandoned.

BACKGROUND OF THE INVENTION

Ectoparasites such as lice and mites cause pruritus or pain in their animal or human hosts. Therapy which simply kills the parasite leaves the host with subcutaneous or intradermal residues which continue to itch for significant time periods after the infestation is extinguished. Furthermore, scratching during and after the episode frequently leads to painful excoriation.

It has now been found that certain ethoxylates exhibit insecticidal and/or ovicidal activity. The same boundaries which delimit the insecticidal properties also include compositions which have a valuable degree of topical anesthetic performance. Although chemically unrelated to any of the conventional anesthetic configurations, these ethoxylates demonstrate topical pharmacologic properties which can be variously characterized as analgesic, anesthetic or antiprurtic.

V. B. Wigglesworth (Journal of Experimental Biology, 21, 3, 4 p. 97 (1945) in a study of transpiration through insect cuticles, reported on the moisture loss of Rhodnius nymphs following treatment with various surfactants. He observed that the ethoxylates of ring compounds had very little action, and that the eight mole ethoxylate of cetyl alcohol was the most effective surfactant be tested, the nymphs losing 48% of body weight in 24 hours. Wigglesworth failed to appreciate that this effect could be adapted to killing insects by an action having no counterpart in higher animals.

Maxwell and Piper (Journal of Economic Entomology, 61, No. 6, Dec. 1968 p. 1633)explored the lethal activity of a large series of ethoxylates against southern house mosquito pupae. They found activity at high dilutions (in the parts per million range), but contrary to Wigglesworth, they reported greatest activity with some ethoxylates of alkylphenols.

In tests against lice and their ova, we have made certain discoveries which were unexpected in light of Maxwell and Piper, and Wigglesworth. We found efficacy only at concentrations several orders of magnitude greater than Maxwell and Piper. Where they reported that short ethylene oxide chain lengths were less effective than 4-6 moles of ethylene oxide, we discovered that the aryl alkyl ethoxylates were best at 1-3 moles of ethylene oxide, and that such compounds were good ovicides but mediocre pediculticides. Certain ethoxylates of aliphatic alcohols were much superior both as insecticides and as ovicides. Moreover, those most effective as toxicants were also found to be most effective as topical anesthetics.

The ethoxylates of this invention are well known as surface active agents have been incorporated in many pharmaceutical and cosmetic preparations as such. For example, polyoxyethylene (4) lauryl ether is 5.5% of a washable coal tar ointment, polyoxyethylene (23) lauryl ether is 8% of an all purpose anionic emulsion for skin application, and a mixture of these two lauryl ethers constitutes 35% of a commercial tar shampoo.

Smith (U.S. Pat. No. 2,666,728) teaches the use up to 51 of a nonionic polyethylene oxide ether of aromatic glycols in a composition for destroying lice. Lindner (U.S. Pat. No. 2,898,267) teaches the use of ethoxylates in emulsifiers for acaricidal compositions.

It is the object of this invention to provide new, safe and effective toxicants for lice and their ova. This and other objects of the invention will become apparent to those skilled in the art from the following detailed description.

SUMMARY OF THE INVENTION

This invention relates to ectoparasiticidal toxicants and a method of controlling ectoparasites and the pain or itch related to infestation. More particularly, the invention relates to the use of certain ethoxylates as toxicants for lice and/or their ova, and for mites, to toxicant compositions containing such ethoxylates and to such ethoxylates as adjunctive therapy to relieve pain or itch.

DESCRIPTION OF THE PREFERRED EMBODIMENTS

The toxicants of the instant invention are certain ethoxylates i.e., certain derivatives of polyoxyethylene $[H(OCH_2CH_2)_nOH]$. The polyoxyethylene glycols per se have not been found to be pediculicidal or ovicidal. For convenience, the polyoxyethylene will hereinafter be referred to as POE and the number of repeating units (n) will be indicated in parenthesis where applicable.

The POE derivatives which exhibit toxicant properties are the alkyl ethers, alkyl ester and block polymers of polyoxypropylene and/or ethylenediamine. Thus, the alkyl or ester moiety, derived from a fatty alcohol or fatty acid respectively, contains 12 to 24 carbon atoms and preferably 12 to 20 carbon atoms. The alkyl moiety is preferably unsubstituted but can, if desired, contain an aryl substituent. The block polymers contain 6 to 100 POE units and 30 to 112 units of polyoxypropylene.

It has been observed that the POE alkyl ethers, alkyl esters and block polymers of polyoxypropylene and/or ethylendiamine require an appropriate hydrophilic-lipophilic balance (HLB) for good activity. In general, the HLB can be about 2.5 to 13.5. The alkyl ethers appeaar to exhibit maximum activity at an HLB in the neighborhood of 9, and the alkyl esters and block polymers at a lower HLB, excepting the alkyl diester, POE (8) dilaurate, having an HLB value of 10.

Exemplary of the POE alkyl ethers of the present invention are POE (1) lauryl ether, POE (2) oleyl ether, POE (2) stearyl ether, POE (3) oleyl ether, POE (3) tridecyl ether, POE (4) myristyl ether, POE (5) oleyl ether, POE (6) tridecyl ether, POE (10) oleyl ether, and the like. POE (1) ethylphenyl ether and POE (3) octylphenyl ether are examples of somewhat effective POE aryl alkyl ethers.

Typical examples of the POE esters include POE (3) oleate, POE (2) laurate, POE (8) dilaurate, and the like. Typical examples of the block polymers include Poloxamer 401, Poloxamer 181 and the like.

One or more of the toxic ethoxylates of the present invention can be incorporated into an active toxicant composition which can be in the form of a liquid, powder, lotion, cream, gel or aerosol spray, or foam as the result or formulation with inert pharmaceutically acceptable carriers by procedures well known in the art. Any pharmaceutically acceptable carrier, whether aqueous or not aqueous, which is inert to the active ingredient can be employed. By inert is meant that the carrier does not have a substantial detrimental effect on the pediculicidal or ovicidal toxicant activity of the active ingredient.

The carrier may also be additive or synergistic to the primary active ingredient.

The active ethoxylate is incorporated into the toxicant composition used to treat the substrate in need of such treatment, believed to be in need of such treatment, or desired to be prophylactically protected in an effective toxicant amount. By such amount is meant the amount which will cause at least 50% of the ectoparasites exposed in the two minute immersion tests described below to die within 24 hours in the case of lice and within 2 weeks in the case of ova. The minimum concentration of ethoxylate in the composition required to provide an effective toxic amount varies considerably depending on the particular ethoxylate, the particular inert pharmaceutically acceptable carrier being employed and any other ingredients which are present. Thus, in one cse a 10% concentration may suffice, while in other cases, concentrations as high as 30 to 40% may be required to obtain an effective toxic dose.

The two minute immersion test referred to above is carried out as follows:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduory cloth patch and this point of time is considered zero hours. Thereafter, the corduory patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lce are then removed and the number of plump, viable eggs and shriveled nonfertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion test, controls are run in identical manners to that described, with room temperature (24° C.) tap water substituted for the sample to be tested. The results of the tests reported are net results.

In the following tables, the results of pediculicidal and ovicidal testing for various toxicants of this invention are set forth. The materials were tested in undiluted form (neat) or in a combination (C) containing 15% (w/w) compound, 25% isopropanol alnd 60% water. For comparative purposes, results achieved with the unmodified ethoxylate, i.e., polyethylene glycol (PEG) and other ethoxylates not within the scope of this invention are also set forth.

TABLE I

Pediculicidal and ovicidal for ethoxylate alcohols having a general structure type $H(OCH_2CH_2)_nOH$.

| | | % Mortality | | | |
|---|---|---|---|---|---|
| | | Periculicidal | | Ovicidal | |
| Compound | n | Neat | C | Neat | C |
| diethylene glycol | 2 | 0 | 5 | 0 | 54 |
| PEG 12 | 12 | 25 | 35 | 35 | 16 |
| PEG 32 | 32 | (1) | 20 | 0(2) | 0 |
| PEG 75 | 75 | (1) | 15 | 0(2) | 14 |

TABLE II

Pediculicidal and ovicidal activity for a series of alkyl ethoxylate ethers

| | | % Mortality | | | |
|---|---|---|---|---|---|
| | | Pediculicidal | | Ovicidal | |
| Compound | LB | Neat | C | Neat | C |
| POE (1) lauryl ether | 3.6 | 100 | 40 | 100(3) | 100 |
| POE (2) oleyl ether | 4.9 | 100 | 10 | 100(3) | 100 |
| POE (2) stearyl ether | 4.9 | 100 | 40 | 100 | 33 |
| POE (3) oleyl ether | 6.6 | 100 | 10 | 100 | 41 |
| POE (3) tridecyl ether | 8 | 100 | 20 | 100 | 100 |
| POE (4) myristyl ether | 8.8 | 100 | 35 | 100(3) | 100 |
| POE (5) oleyl ether | 8.8 | 100 | 15 | 100 | 8.3 |
| POE (4) lauryl ether | 9.5 | 100 | 30 | 100 | 83 |
| POE (6) tridecyl ether | 11 | 100 | 30 | 100 | 0 |
| POE (6.5) tridecyl ether | 11.6 | 100 | 15 | 100 | 34 |
| POE (6) lauryl thioether | 11.6 | 100 | 20 | 100 | 0 |
| POE (10) oleyl ether | 12.4 | 100 | 10 | 5 | 68 |
| POE (7) lauryl ether | 12.5 | 100(4) | 0 | 100(4) | 36 |
| POE (8) lauryl thioether | 13.4 | 75 | 20 | 67 | 0 |
| POE (9) lauryl ether | 13.6 | 100 | 20 | 100(3) | 19 |
| POE (10) lauryl thioether | 13.9 | 15 | 5 | 30 | 0 |
| POE (12) lauryl ether | 14.5 | 20 | 5 | 100 | 0 |
| POE (20) isohexadecyl ether | 15.7 | (1) | 0 | 11(2) | 2 |
| POE (23) layryl ether | 36.9 | (1) | 0 | 69(2) | 3 |

TABLE III

Pediculicidal and ovicidal activity for some arylalkyl ethoxylate ethers.

| | | % Mortality | | | |
|---|---|---|---|---|---|
| | | Pediculicidal | | Ovicidal | |
| Compound | HLB | Neat | C | Neat | C |
| POE (1) octylphenyl ether | 3.6 | 80 | 10 | 100(3) | 66 |
| POE (3) octylphenyl ether | 7.8 | 15 | 5 | 82(3) | 34 |
| POE (10) nonylphenyl ether | 13.4 | 20 | 5 | 82(3) | 0 |

TABLE IV

Pediculicidal and ovicidal activity for ethoxylate mono and diesters.

| | | % Mortality | | | |
|---|---|---|---|---|---|
| | | Pediculicidal | | Ovicidal | |
| Compound | HLB | Neat | C | Neat | C |
| POE (2) oleate | 3.5 | 70 | 75 | 100(3) | 14 |
| POE (2) laurate | 6.0 | 25 | 20 | 100(3) | 6.5 |
| POE (8) dioleate | 7.2 | 40 | 0 | 7.3 | 26 |
| POE (2) laurate | 7.4 | 95 | 65 | 100(3) | 8.3 |
| POE (8) distearate | 7.8 | (1) | 40 | (1) | 23 |
| POE (4) laurate | 8.6 | 10 | 15 | 14 | 5.9 |

TABLE IV-continued
Pediculicidal and ovicidal activity for ethoxylate mono and diesters.

| | | % Mortality | | | |
|---|---|---|---|---|---|
| | | Pediculicidal | | Ovicidal | |
| Compound | HLB | Neat | C | Neat | C |
| POE (4) sorbitol septaoleate | 9 | 5 | 20 | 77 | 21 |
| POE (8) dilaurate | 10 | 80 | 10 | 23 | 38 |
| POE (12) dilaurate | 10.6 | (1) | 40 | (1) | 24 |
| POE (20) distearate | 15 | (1) | 0 | (1) | 0 |
| POE (300) stearate | 18.8 | (1) | 0 | (1) | 5 |

TABLE V
Pediculicidal and ovicidal activity for ethoxylate block polymers having the general structure type outlined for each section.

(A) based on structure type

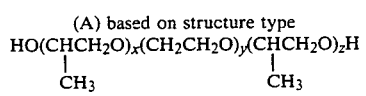

| | | | | % Mortality | | | |
|---|---|---|---|---|---|---|---|
| | | | | Pediculicidal | | Ovicidal | |
| x | y | z | HLB | Neat | C | Neat | C |
| 18 | 14 | 18 | 4.5 | 10 | 0 | 56 | 4.8 |
| 12 | 23 | 32 | 8.4 | 5 | 0 | 0 | 15 |
| 7 | 22 | 7 | 10.8 | 10 | 0 | 0 | 41 |

(B) based on structure type

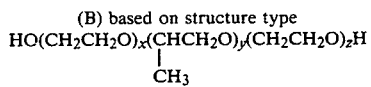

| | | | | % Mortality | | | |
|---|---|---|---|---|---|---|---|
| | | | | Pediculicidal | | Ovicidal | |
| x | y | z | HLB | Neat | C | Neat | C |
| 3 | 30 | 3 | 3 | 10 | 0 | 70 | 0 |
| 13 | 67 | 13 | 4 | — | 10 | 0(2) | 1.2 |
| 6 | 67 | 6 | 5 | 55 | 0 | 80 | 84 |
| 8 | 30 | 8 | 7 | 0 | 50 | 8.4 | 0 |
| 21 | 67 | 21 | 8 | (1) | 10 | 0(2) | 4.5 |
| 13 | 30 | 13 | 15 | 5 | 20 | 0 | 17 |
| 38 | 54 | 38 | 15 | (1) | 0 | 0(2) | 19 |
| 122 | 47 | 122 | 27.5 | (1) | 40 | (1) | 4.5 |

(C) based on structure type

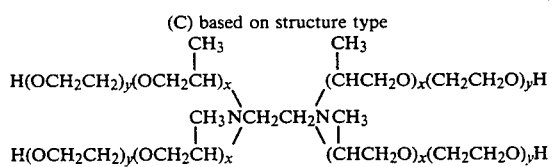

| | | | % Mortality | | | |
|---|---|---|---|---|---|---|
| | | | Pediculicidal | | Ovicidal | |
| x | y | HLB | Neat | C | Neat | C |
| 18 | 2 | 2 | 5 | 20 | 79 | 0 |
| 12 | 2 | 3 | 45 | 0 | 73(3) | 11 |
| 21 | 7 | 3.5 | 30 | 0 | 100(3) | 53 |
| 26 | 8 | 5 | 5 | 0 | 100(3) | 49 |
| 13 | 4 | 7 | 0 | 20 | 58 | 0 |
| 26 | 24 | 13 | 85 | 0 | — | 20 |
| 8 | 7 | 16 | 0 | 20 | 0 | 28 |

Notes to Tables I-V
(1) solid - could not be tested at 100%
(2) 50% (w/w) in ethanol
(3) pad noted to be coated with compound at conclusion of test
(4) 90% (w/w) in water The pediculicidal activity of various compounds set forth in Table II as a functiin of concentratin was determined in a diluted system containing 25% isopropanol and water q.s. The results are shown in Table VI.

TABLE VI

| Concentration, % (w/w) | | Mortality, % |
|---|---|---|
| A. POE (1) lauryl ether | HLB = 3.6 | |
| 10 | | 55 |
| 15 | | 40 |
| 20 | | 80 |
| 30 | | 85 |
| 40 | | 80 |
| 50 | | 95 |
| B. POE (2) oleyl ether | HLB = 4.9 | |
| 10 | | 30 |
| 15 | | 10 |
| 20 | | 35 |
| 30 | | 15 |
| 40 | | 20 |
| 50 | | 35 |
| C. POE (2) stearyl ether | HLB = 4.9 | |
| 10 | | 0 |
| 15 | | 40 |
| 20 | | 80 |
| 30 | | 50 |
| 40 | | 100 |
| 50 | | 100 |
| D. POE (3) oleyl ether | HLB = 6.6 | |
| 15 | | 10 |
| 20 | | 15 |
| 30 | | 60 |
| 40 | | 70 |
| 50 | | 100 |
| 60 | | 100 |
| E. POE (3) tridecyl ether | HLB = 8 | |
| 10 | | 25 |
| 15 | | 20 |
| 20 | | 95 |
| 30 | | 95 |
| 40 | | 100 |
| 50 | | 100 |
| F. POE (4) myristyl ether | HLB = 8 | |
| 10 | | 75 |
| 15 | | 35 |
| 20 | | 90 |
| 30 | | 100 |
| 40 | | 100 |
| 50 | | 100 |
| G. POE (4) lauryl ether | HLB = 9.5 | |
| 10 | | 15 |
| 15 | | 30 |
| 20 | | 55 |
| 30 | | 80 |
| 40 | | 85 |
| 50 | | 60 |
| H. POE (6) tridecyl ether | HLB = 11 | |
| 10 | | 40 |
| 15 | | 30 |
| 20 | | 65 |
| 30 | | 75 |
| 40 | | 35 |
| 50 | | 55 |
| I. POE (6.5) tridecyl ether | HLB = 11.6 | |
| 15 | | 15 |
| 20 | | 25 |
| 30 | | 5 |
| 40 | | 35 |
| 50 | | 30 |
| 60 | | 60 |
| J. POE (7) lauryl ether | HLB = 12.5 | |
| 15 | | 0 |
| 20 | | 10 |
| 30 | | 20 |
| 40 | | 20 |
| 50 | | 35 |
| 60 | | 40 |
| K. POE (9) lauryl ether | HLB = 13.6 | |
| 15 | | 20 |
| 20 | | 25 |
| 30 | | 15 |
| 40 | | 25 |
| 50 | | 70 |
| 60 | | 50 |
| L. POE (12) lauryl ether | HLB = 14.5 | |

TABLE VI-continued

| Concentration, % (w/w) | Mortality, % |
|---|---|
| 15 | 5 |
| 40 | 0 |
| 50 | 15 |
| 60 | 30 |
| 70 | 45 |
| M. POE (23) lauryl ether HLB = 16.9 | |
| 15 | 0 |
| 20 | 0 |
| 30 | 0 |
| 40 | 0 |
| 50 | 0 |
| 60 | 5 |

The pediculicidal activity of two ethoxylated alkyl ethers as a function of concentration when diluted with water was determined and the results are set forth in Table VII.

TABLE VII

| Concentration, % (w/w) | Mortality, % |
|---|---|
| A. POE (2) oleyl ether HLB = 4.9 | |
| 5 | 0 |
| 10 | 10 |
| 20 | 35 |
| 30 | 90 |
| 40 | 100 |
| 60 | 100 |
| 80 | 100 |
| 100 | 100 |
| B. POE (4) lauryl ether HLB = 9.5 | |
| 5 | 5 |
| 10 | 5 |
| 15 | 45 |
| 20 | 100 |
| 80 | 100 |
| 90 | 100 |
| 100 | 100 |

The ovicidal activity of various compounds set forth in Table II as a function of concentration was determined in a diluted system containing 25% isopropanol and water q.s. The rsults are shown in Table VIII.

TABLE VIII

| Concentration, % (w/w) | % Mortality |
|---|---|
| A. POE (1) lauryl ether HLB = 3.6 | |
| 1 | 100 |
| 3 | 100 |
| 5 | 100 |
| 7 | 100 |
| 9 | 100 |
| B. POE (3) tridecyl ether HLB = 8 | |
| 10 | 100 |
| 15 | 100 |
| 20 | 100 |
| 30 | 100 |
| 40 | 100 |
| C. POE (4) myristyl ether HLB = 8.8 | |
| 10 | 27 |
| 15 | 100 |
| 20 | 100 |
| 30 | 92 |
| 40 | 100 |
| 50 | 100 |
| D. POE (6) tridecyl ether HLB = 11 | |
| 10 | 0 |
| 15 | 0 |
| 20 | 16 |
| 30 | 44 |
| 40 | 14 |
| 50 | 3 |
| E. POE (12) lauryl ether HLB = 14.5 | |
| 15 | 0 |

TABLE VIII-continued

| Concentration, % (w/w) | % Mortality |
|---|---|
| 30 | 0 |
| 40 | 0.2 |
| 50 | 5 |
| 60 | 2 |
| 70 | 0 |
| F. POE (23) lauryl ether HLB = 16.9 | |
| 15 | 3 |
| 20 | 10 |
| 30 | 4 |
| 40 | 5 |
| 50 | 0 |
| 60 | 5 |

Table IX reflects the resulting pediculicidal and ovicidal activity of a 15% (w/w) concentration of POE (4) lauryl ether with variation of isopropanol and water content

TABLE IX

| % w/w isopropanol | % w/w water | % Mortality Pediculicidal | % Mortality Ovicidal |
|---|---|---|---|
| 25 | 60 | 30 | 83 |
| 20 | 65 | 30 | 21 |
| 15 | 70 | 15 | 19 |
| 10 | 75 | 15 | 15 |
| 5 | 80 | 95 | 100 |
| 1 | 84 | 20 | 100 |
| 0 | 85 | 45 | 10 |

As can be seen from Table IX, the 15% concentration of POE (4) lauryl ether exhibited synergistic pediculicidal activity when the isopropanol was about 1-5%.

The most effective toxicants of this invention have also been found to exhibit topical anesthetic activity. Thus, for example, one drop of 5% aqueous POE (4) lauryl ether caused an onset of corneal anesthetic action in about 5-8 minutes with a duration of about 0.5-4 hours (average four tests was two hours) in a modified Cole and Rose rabbit eye iritiation test (J. Lab. & Clin. Med. 15:239, 1929). In contrast, POE (23) lauryl ether did not exhibit any activity in the same test. In general, the preferred alkyl ethers exhibit anesthetic analgesic or antipruritic activity at concentrations of at least 1% and are preferably employed for this purpose at about 1-10%.

The miticidual activity of some of the instant toxicants was determined as follows. Into a one cubic foot chamber, held at room temperature, is placed a covered microscope depression slide containing ten adult mixed sex mites, Psoroptes equi var. cuniculi. The slide is positioned at a distance of ten inches horizontally and four inches below the activator of a mechanical spray device and uncovered. The mechanical pump spray device delivers 50 micrograms of sample per depression of the activator. The sample to be tested, maintained at room temperature, is shaken until homogeneous and placed in the mechanical pump spray device. The printed activator is depressed twice, releasing 100 micrograms of spray mist into the closed chamber. The mist is allowed to settle and the slide containing the mites is removed and covered. This point of time is considered zero hours. The covered slide is then held at room temperature for 24 hours. Miscroscopic observations are noted at 0, 1, 3, and 24 hours post treatment. Controls are run in an identical manner as that described using water or the diluting agent, and net mortality results are reported.

Table X shows the miticidal activity of a 50% (w/w) concentration of the named compounds in disopropanol.

TABLE X

| Compound | HLB | Miticidal Activity, % |
| --- | --- | --- |
| POE (1) lauryl ether | 3.6 | 100 |
| POE (2) oleyl ether | 4.9 | 80 |
| POE (4) myristyl ether | 8.8 | 100 |
| POE (4) lauryl ether | 9.5 | 100 |
| POE (6) tridecyl ether | 11 | 90 |
| POE (10) oleyl ether | 1.4 | 100 |
| POE (12) lauryl ether | 14.5 | 100 |

As noted, various end use formulations can be prepared. Some typical formulations are set forth and the amounts recited are percentages by weight:

| Liquid pediculicide and ovicide suitable for mechanical spray application or inunction. | |
| --- | --- |
| POE (8) dilaurate | 15 |
| Isopropanol | 60 |
| Water | 25 |
| Liquid pediculicide and ovicide shampoo | |
| POE (4) lauryl ether | 26.0 |
| POE (23) lauryl ether | 7.7 |
| Isopropanol | 7.7 |
| Benzalkonium chloride | 0.2 |
| Water | 58.4 |
| Ovicidal powder | |
| POE (3) tridecyl ether | 3 |
| Pyrophyllite | 97 |
| Pediculicidal and ovicidal powder | |
| POE (1) lauryl ether | 10 |
| Prophyllite | 90 |
| Pediculicidal Stick | |
| POE (2) oleyl ether | 15.0 |
| Sodium stearate | 8.0 |
| Sorbitol | 3.5 |
| Isopropanol | 25.0 |
| Ethanol | 39.0 |
| Water | 9.5 |
| Pediculicidal and ovicidal quick breaking aerosol foam | |
| POE (4) lauryl ether | 20 |
| Water | 72 |
| Isobutane | 8 |
| Pediculicidal and ovicidal gel | |
| POE (2) oleyl ether | 15.0 |
| Isopropanol | 25.0 |
| Carbomer 940 | 0.5 |
| Triethanolamine | 0.36 |
| Water | 59.12 |

As noted, various changes and modifications can be made in the instant invention without departing from the spirit and scope thereof. The various embodiments disclosed herein were made for the purpose of further illustrating the invention but were not intended to limit it. Throughout this specification and claims, all temperatures are in degrees Centigrade and all parts and percentages are by weight unless otherwise indicated.

We claim:

1. A method of controlling ectoparasites or their ova which comprise applying to a human or animal host in need of such control, an effective toxic amount of at least one derivative of polyoxyethylere having an HLB of about 2.5–13.5, said derivative being a block copolymer of polyoxyethylene and polyoxypropylene or ethlylenediamine.

2. The method of claim 1 wherein said derivative is employed in combination with an inert pharmaceutically acceptable carrier.

3. The method of claim 2 wherein said carrier is an aqueous carrier.

4. The method of claim 1 wherein said ectoparasites are lice or mites.

5. The method of claim 1 wherein said block polymer is a block copolymer of polyoxyethylene and polyoxyproplene.

6. The method of claim 5 wherein said block polymer containing 6 to 100 polyoxyethylene units and 30 to 120 units of polyoxypropylene.

7. The method of claim 6 wherein said block polymer contains 2 to 24 polyoxyethylene units and 8 to 26 polyoxypropylene units.

8. The method of claim 6 wherein said block copolymer is

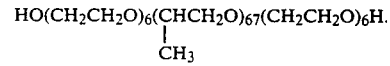

9. The method of claim 1 wherein said block copolymer is of the formula

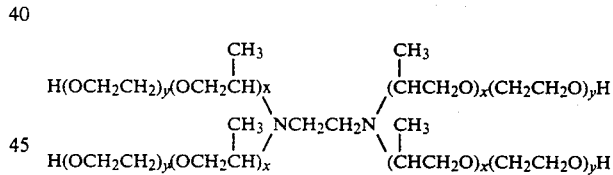

where x is 13 to 26 and y is 2 to 24.

10. The method of claim 9 wherein x is 21 and y is 7.
11. The method of claim 9 wherein x is 26 and y is 8.

* * * * *